(12) United States Patent
König

(10) Patent No.: US 11,448,532 B2
(45) Date of Patent: Sep. 20, 2022

(54) SENSOR DEVICE, METHOD FOR OPERATING A SENSOR DEVICE AND ELECTRONIC ASSEMBLY COMPRISING A SENSOR DEVICE

(71) Applicant: TDK Corporation, Tokyo (JP)

(72) Inventor: Matthias König, Freising (DE)

(73) Assignee: TDK CORPORATION, Tokyo (JP)

( * ) Notice: Subject to any disclaimer, the term of this patent is extended or adjusted under 35 U.S.C. 154(b) by 753 days.

(21) Appl. No.: 16/382,030

(22) Filed: Apr. 11, 2019

(65) Prior Publication Data

US 2019/0316941 A1  Oct. 17, 2019

(30) Foreign Application Priority Data

Apr. 12, 2018 (DE) .......................... 102018108723.3

(51) Int. Cl.
| | |
|---|---|
| *G01D 11/24* | (2006.01) |
| *G01N 27/14* | (2006.01) |
| *G01N 27/407* | (2006.01) |
| *G01J 5/04* | (2006.01) |
| *H05B 3/12* | (2006.01) |
| *H05B 3/26* | (2006.01) |
| *G01N 33/00* | (2006.01) |

(52) U.S. Cl.
CPC .............. *G01D 11/245* (2013.01); *G01J 5/04* (2013.01); *G01N 27/14* (2013.01); *G01N 33/0027* (2013.01); *G01N 33/0031* (2013.01); *G01N 33/0032* (2013.01); *H05B 3/12* (2013.01); *H05B 3/26* (2013.01)

(58) Field of Classification Search
None
See application file for complete search history.

(56) References Cited

U.S. PATENT DOCUMENTS

| | | | | |
|---|---|---|---|---|
| 4,654,624 | A * | 3/1987 | Hagan | G01N 27/12 436/160 |
| 6,344,174 | B1 * | 2/2002 | Miller | G01N 27/16 422/90 |
| 6,528,019 | B1 * | 3/2003 | Moos | G01N 27/12 422/50 |
| 9,989,409 | B2 * | 6/2018 | Van Der Wiel | G01J 5/045 |

(Continued)

FOREIGN PATENT DOCUMENTS

| | | | | |
|---|---|---|---|---|
| DE | 10246051 | A1 * | 4/2004 | ........... G01N 33/004 |
| DE | 102013104043 | A1 * | 10/2014 | ........... G01D 11/245 |

(Continued)

OTHER PUBLICATIONS

Texas Instruments, "Infrared Thermopile Sensor in Chip-Scale Package," TMP006, May 2011, pp. 1-20.

*Primary Examiner* — Joseph M. Pelham
(74) *Attorney, Agent, or Firm* — Slater Matsil, LLP

(57) ABSTRACT

A sensor device, a method for operating a sensor device and an electronic assembly comprising a sensor device are disclosed. In an embodiment a sensor device includes a first sensor unit and a second sensor unit in a common housing, wherein each of the first and second sensor units comprises a heater element and a temperature sensor element, wherein the housing comprises a cover element having an opening, the cover element covering the first sensor unit, and wherein the opening is arranged over the second sensor unit.

20 Claims, 5 Drawing Sheets

(56) References Cited

U.S. PATENT DOCUMENTS

| | | | |
|---|---|---|---|
| 9,995,593 B2* | 6/2018 | Badeja | G01D 3/036 |
| 10,627,379 B2* | 4/2020 | Zanella, Sr | G01N 27/16 |
| 10,670,548 B2* | 6/2020 | Ostrick | G01D 11/245 |
| 2005/0028580 A1* | 2/2005 | Bauer | G01N 27/18 73/25.03 |
| 2013/0093037 A1* | 4/2013 | Kirihara | G01J 5/0831 257/435 |
| 2013/0327944 A1* | 12/2013 | Ernst | G01J 5/061 219/209 |
| 2014/0208828 A1 | 7/2014 | Von Waldkirch | |
| 2016/0123816 A1 | 5/2016 | Pei et al. | |
| 2016/0349201 A1* | 12/2016 | Graunke | G01N 27/128 |
| 2017/0343502 A1 | 11/2017 | Ali et al. | |
| 2018/0045663 A1* | 2/2018 | Ahn | G01N 33/0031 |
| 2018/0059021 A1* | 3/2018 | Yeh | H05K 5/0017 |
| 2018/0100842 A1* | 4/2018 | Ahn | G01N 33/0027 |
| 2018/0136182 A1* | 5/2018 | Wang | G01N 33/0036 |
| 2019/0316967 A1* | 10/2019 | Schieferdecker | G01J 5/04 |
| 2020/0049645 A1* | 2/2020 | Kim | G01N 27/128 |
| 2020/0049647 A1* | 2/2020 | König | G01N 27/16 |
| 2020/0088669 A1* | 3/2020 | König | G01N 25/18 |
| 2021/0088464 A1* | 3/2021 | Rabe | G01N 33/0014 |
| 2021/0341405 A1* | 11/2021 | Swager | C07C 29/48 |
| 2021/0396696 A1* | 12/2021 | Hornung | G01N 25/4826 |
| 2022/0120701 A1* | 4/2022 | Udrea | G01N 33/0027 |

FOREIGN PATENT DOCUMENTS

| | | | |
|---|---|---|---|
| EP | 0076935 A2 | 4/1983 | |
| EP | 3591389 A1 * | 1/2020 | G01N 1/24 |
| EP | 3705885 A1 * | 9/2020 | G01N 33/0031 |
| WO | WO-0043765 A1 * | 7/2000 | G01N 27/16 |
| WO | 0118500 A1 | 3/2001 | |
| WO | WO-2006037283 A1 * | 4/2006 | G01N 27/16 |

\* cited by examiner

SENSOR DEVICE, METHOD FOR OPERATING A SENSOR DEVICE AND ELECTRONIC ASSEMBLY COMPRISING A SENSOR DEVICE

CROSS-REFERENCE TO RELATED APPLICATIONS

This application claims the priority to German patent application 102018108723.3, filed on Apr. 12, 2018, which application is hereby incorporated herein by reference.

TECHNICAL FIELD

Embodiments of the present invention relate to a sensor device, in particular to a sensor device comprising the functionalities of a gas sensor and an infrared sensor, a method for operating such sensor device and an electronic assembly comprising such sensor device.

BACKGROUND

There are more and more applications for miniaturized sensors, for example, in smartphones. Such sensors typically have a human counterpart, as for instance eyes/camera, ears/microphone, sense of touch/touchscreen, sense of balance/gyroscope. However, the sense of temperature and the sense of smelling are usually not realized in smartphones. The sense of temperature is missing, because the smartphone device itself produced heat, for example, by the ICs (e.g., the processor) inside the cover, and thus is heated by itself. Therefore, it is not possible to measure the surrounding temperature with a conventional temperature sensor as the temperature sensor reading will only correspond to an arbitrary smartphone temperature. The sense of smelling or, in technical terms, a gas sensor, is missing due to technologic issues like power consumption.

SUMMARY

Embodiments provide a sensor device, in particular a sensor device that comprises the functionalities of a gas sensor and an infrared sensor. Further embodiments provide a method for operating such sensor device. Yet other embodiments provide an electronic assembly comprising such sensor device.

According to at least one embodiment, a sensor device comprises a first sensor unit and a second sensor unit. The sensor device can be operated in at least a first mode of operation and a second mode of operation which is different from the first mode of operation. In particular, the sensor device can be operated as a gas sensor in the first mode of operation and as an infrared sensor in the second mode of operation. The first mode of operation can be used to gather information about a gas, for instance the composition and/or the concentration, wherein the second mode of operation can be used to gather information about the infrared radiation emitted by at least a part of an object facing the sensor device and thus about the temperature of the object. Both the first and second sensor units are operated in both modes of operation, respectively. In other words, a combined operation of the first and second sensor units provides measurement readings in the first mode of operation, and another combined operation of the first and second sensor units provides measurement readings in the second mode of operation.

According to at least one further embodiment, a method for operating a sensor device comprises the operation of the first and second sensor units in the first mode of operation and, at another time, the operation of the first and second sensor units in the second mode of operation.

According to at least one further embodiment, an electronic assembly comprises a carrier carrying an electronic component and a sensor device.

The previous and the following description are related to the sensor device, the method for operating the sensor device and the electronic assembly comprising the sensor device, respectively.

According to a further embodiment, at least one of the sensor units and preferably each of the sensor units comprises a heater element and a temperature sensor element. The heater element of a sensor unit is preferably used in the first mode of operation. When operated, the heater of a sensor unit increases the temperature of that sensor unit or of at least a part of that sensor unit to a temperature that is required for the first mode of operation. Most preferably, in the first mode of operation the heater element of each of the sensor units is operated to heat the respective sensor unit to the same temperature as compared to the respective other sensor unit, while in the second mode of operation the heater element of each of the sensor units is not operated to heat the respective sensor unit. In other words, neither of the sensor units is substantially heated by its respective heater element in the second mode of operation. Particularly preferably, the mode of operation can be chosen by either operating the heater elements of the sensor units or not operating the heater elements of the sensor units. Alternatively, also in the second mode of operation the heater elements of the sensor units can be operated, for example, by heating the sensor units to the same or to another temperature as compared to the first mode of operation. For example, by operating the heater elements in the second mode of operation, the sensor units can be heated to a temperature at which the temperature sensor elements are most sensitive.

The sensor device can have electrical contacts for contacting the sensor units and/or for measuring at least one electrical property of each of the sensor units. The electrical property can be, for example, an electrical resistance, an electrical current and/or an electrical voltage. Measuring the at least one electrical property of each of the sensor units and comparing the respective measured electrical properties of the sensor units can provide measurement signals in both modes of operation, respectively. For example, the sensor units can be part of a Wheatstone Bridge.

According to a further embodiment, at least one of the sensor units, in particular the first sensor unit, is embodied as a pellistor. There are two types of pellistors, namely catalytic pellistors and thermal conductivity (TC) pellistors, which can be distinguished by their different operating modes. A sensor unit embodied as catalytic pellistor comprises a catalyst element and, in the first mode of operation, works by burning a gas to be examined (target gas) at the catalyst element, which is heated by the heater of the sensor unit. The additional heat that is generated by the gas combustion process can be detected and preferably can be used to produce a sensor signal that is proportional to the gas concentration. In the case of a TC pellistor, the catalyst element is missing. The pellistor is then measuring the heat conductivity of the gas to be examined, since the target gas changes the heat conductivity of the surrounding air.

The catalyst element can comprise a metal oxide. The metal oxide can for instance comprise Al and/or Pt. For example, the catalyst element can comprise or consist of platinum oxide and/or aluminum oxide or aluminum oxide mixed with platinum.

According to a further embodiment, the second sensor unit is embodied similarly to the first sensor unit, but without the catalyst element. In particular, the second sensor unit can comprise a heater element and a temperature sensor element similar to the heater element and the temperature sensor element of the first sensor unit. In the first mode of operation, the second sensor unit can be operated in the same way as the first sensor unit. In particular, the second sensor unit can be heated similarly to the first sensor unit, for example, by using the same or substantially the same electrical current. In this way, in the first mode of operation the second sensor unit is operated as a reference sensor. Consequently, the first sensor unit can be an active sensor unit, in particular in case of a catalytic pellistor, while the second sensor unit can work as a compensator, having no catalyst element. Advantageously, the sensor device then only reacts to gas concentration changes, while other environmental changes as for instance a change of humidity and/or a change of the ambient temperature, will be cancelled.

According to a further embodiment, in the second mode of operation the second sensor unit is heated by infrared radiation emitted by an external object, while the first sensor unit is blocked from that infrared radiation. Consequently, in the second mode of operation, the first sensor unit can be operated as a reference sensor so that, similar to the first mode of operation, environmental changes potentially distorting the measurement can be cancelled out.

According to a further embodiment, the sensor device comprises a common housing for the first and second sensor unit. In other words, both the first and second sensor unit are arranged in the common housing. The housing preferably completely encloses the first and second sensor unit except for an opening in the housing. In other words, the housing has an interior space in which the sensor units are arranged, wherein the interior space is connected to the environment only or at least substantially only through the opening. Preferably, the housing has no further opening. The gas to be examined in the first mode of operation can enter the housing through the opening.

According to a further embodiment, the opening is arranged over the second sensor unit. This can in particular imply that infrared radiation emitted from an external object, which is placed in front of the opening, can enter the housing through the opening and can be irradiated onto the second sensor unit, thereby increasing the temperature of the second sensor unit. The first sensor unit can be covered by a part of the housing arranged between the first sensor unit and the object and thus can be blocked from that infrared radiation. Preferably, the housing comprises a cover element having the opening, wherein the cover element completely covers the first sensor element, while the opening is arranged over the second sensor element.

According to a further embodiment, the temperature sensor element of at least one of the sensor units and preferably of each of the sensor units comprises an NTC (negative temperature coefficient) or PTC (positive temperature coefficient) material. Preferably, the temperature sensor element of at least one of the sensor units and preferably of each of the sensor units comprises a noble metal and/or one or more metal oxides. For example, the noble metal comprises or is Pt.

According to a further embodiment, the heater element of at least one of the sensor units and preferably of each of the sensor units is embodied as a heating filament or heating wire and, in particular, as a heating resistance. Preferably, the heater element of at least one of the sensor units and preferably of each of the sensor units comprises or is made of a noble metal as, for example, Pt. Other metals, for example W, are also possible in addition or alternatively.

According to a further embodiment, the heater element of at least one of the sensor units and preferably of each of the sensor units is the temperature sensor element. In other words, the heater element and the temperature sensor element are one and the same component. Alternatively, the heater element and the temperature sensor element can be embodied as two different components.

According to a further embodiment, the sensor device comprises a common substrate carrying both the first and second sensor unit. Preferably, the substrate comprises silicon. The temperature sensor element of at least one of the sensor units and preferably of each of the sensor units can be arranged in a membrane, which is arranged on the substrate. Alternatively or additionally, in case the temperature sensor element and the heater element are different components, also the heater element of at least one of the sensor units and preferably of each of the sensor units can be arranged in the membrane. The catalyst element of the first sensor unit can be arranged on the membrane in order to have contact to the surrounding gas atmosphere. The membrane of at least one of the sensor units and preferably of each of the sensor units comprises or is made of an electrically insulating material, for instance silicon oxide and/or silicon nitride, and at least partly encloses the heater element and/or the temperature element. The substrate and/or the membrane with the components arranged in the membrane can be manufactured by standard MEMS (microelectromechanical systems) technology, thereby providing small dimensions and a high degree of integration.

According to a further embodiment, the electronic assembly comprises the electronic component and the sensor device on a common carrier, wherein the second sensor unit faces a surface of the electronic component through the opening in the housing. The electronic component can comprise an active electronic component. Furthermore, the electronic component can comprise a heat sink attached to the active electronic component. The surface of the electronic component faced by the second sensor unit can be a surface of the active electronic component and/or of the heat sink. Thus, the sensor device can be used to measure information about a gas in the vicinity of the electronic component in the first mode of operation and information about a temperature of the electronic component in the second mode of operation.

As described above, the sensor device can be embodied as an infrared/gas combo sensor. In particular, the sensor device can be based on MEMS technology. The sensor device or the electronic assembly comprising the sensor device can be used, for example, in a smartphone or other devices, for example, devices used in home automatization applications and automotive applications. In particular, the sensor device described herein can be useful whenever gas and temperature measurements are needed. In the case of gas measurements, the temperature can also be a very important parameter. For example, when gas concentrations are used for comfort estimations, the temperature is an important parameter, too. By way of example, the sensor device can be useful in an air conditioning system, since on the one hand the regulation electronics needs to know when the air needs to be exchanged, which means using the gas sensor mode of operation, while on the other hand the regulation electronics also needs to know if the heating or cooling must be turned on, which means using the infrared sensor mode of operation.

BRIEF DESCRIPTION OF THE DRAWINGS

Further features, advantages and expediencies will become apparent from the following description of exemplary embodiments in conjunction with the figures.

In the figures, elements of the same design and/or function are identified by the same reference numerals. It is to be understood that the embodiments shown in the figures are illustrative representations and are not necessarily drawn to scale.

DETAILED DESCRIPTION OF ILLUSTRATIVE EMBODIMENTS

In the following, specific details are set forth, such as features of the sensor device, a method for operating the sensor device and an electronic assembly comprising a sensor device as well as advantageous effects thereof, in order to provide a thorough understanding of embodiments of the invention. It will be apparent to one skilled in the art that embodiments of the invention may be practiced without these specific details.

Figure 1A:
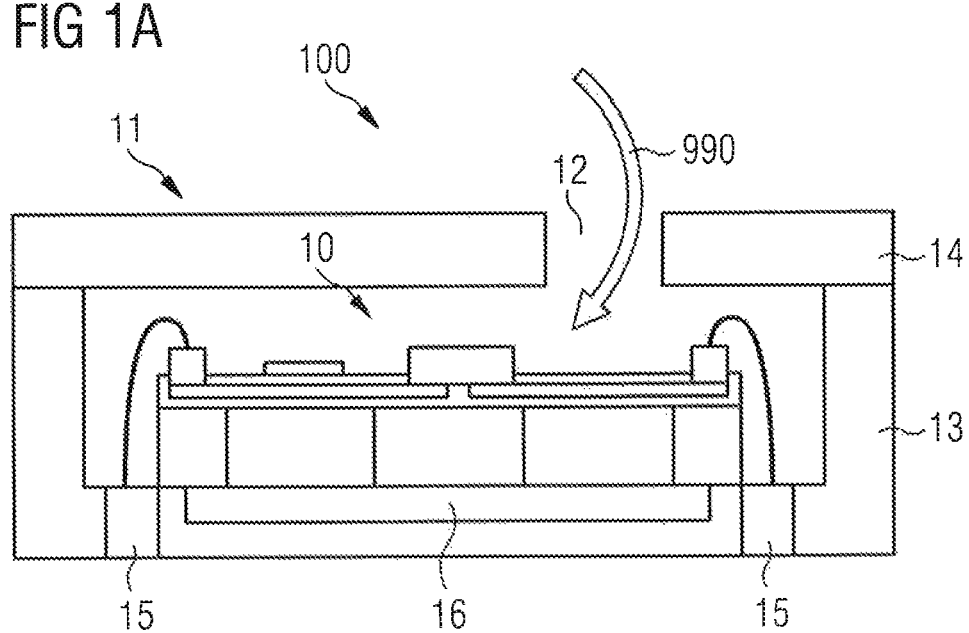
FIGS. 1A-1D illustrate a sensor device operated in different modes of operation according to an embodiment.
Figure 1B:
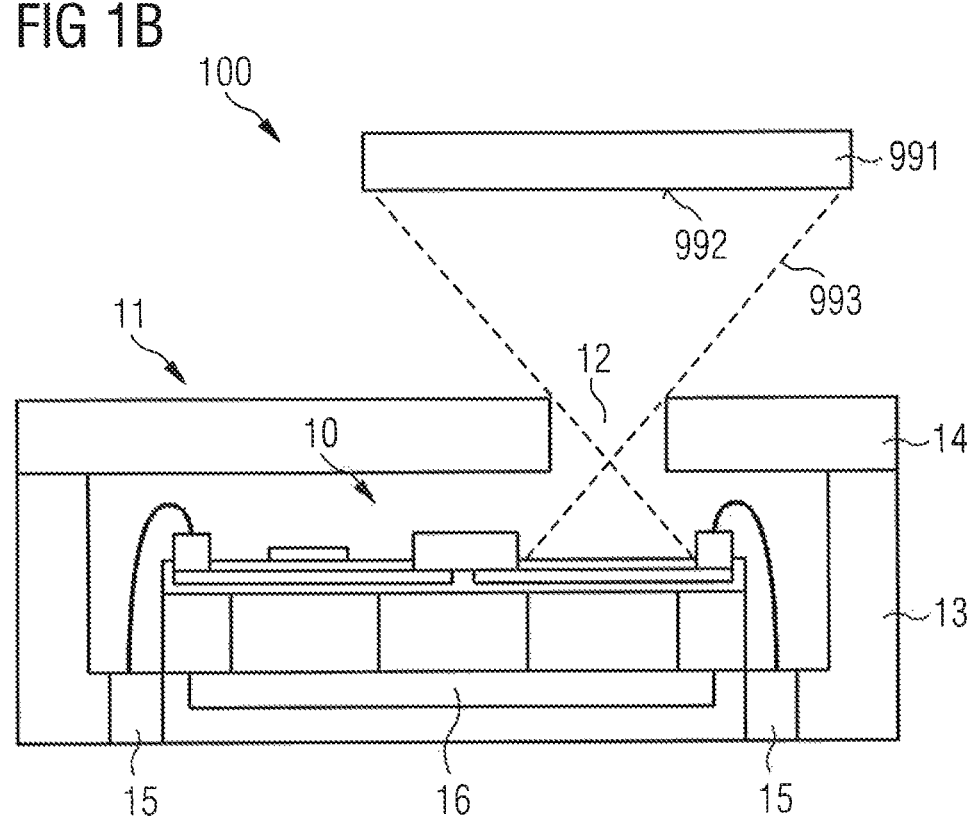
Figure 1C:
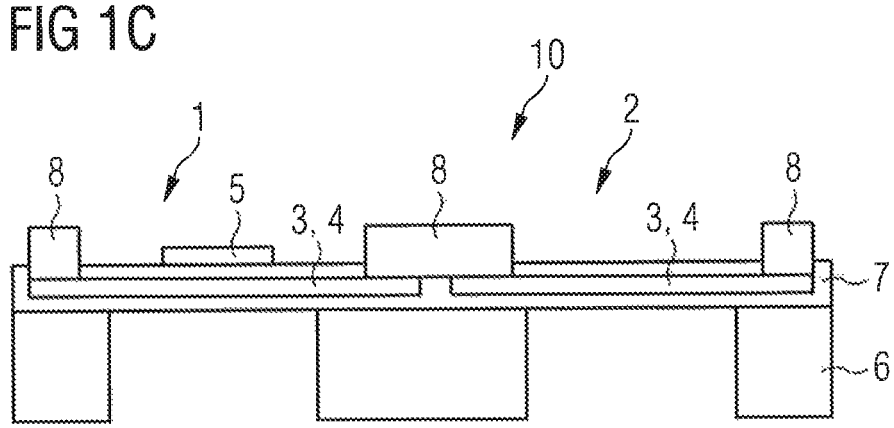
Figure 1D:
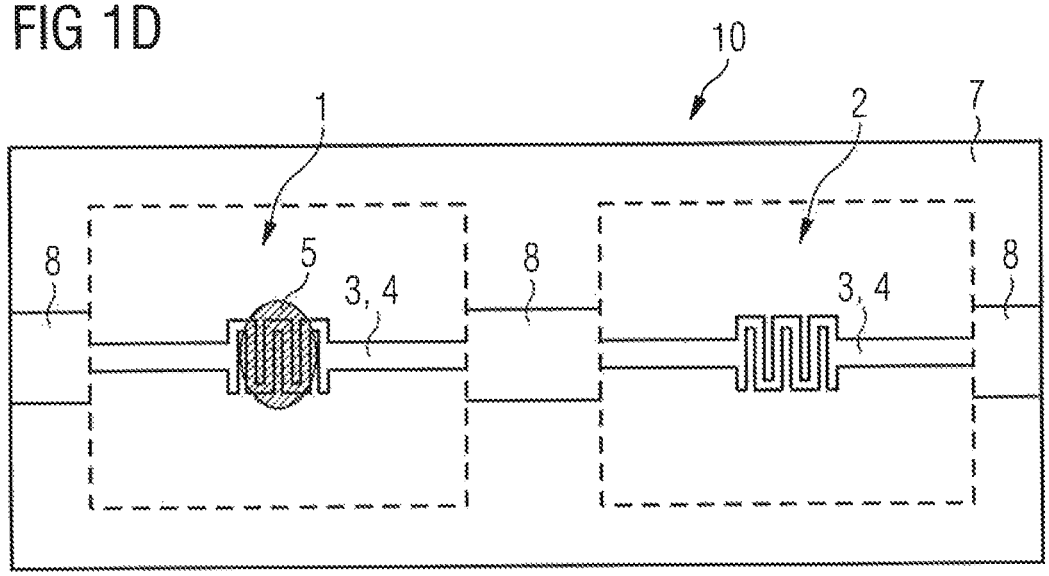

In connection with FIGS. 1A to 1D a sensor device 100 according to an embodiment in different modes of operation is illustrated. In particular, FIG. 1A serves to illustrate the sensor device 100 comprising a sensor arrangement 10 in a common housing 11 operated in a first mode of operation, wherein FIG. 1B serves to illustrate the sensor device 100 operated in a second mode of operation. FIGS. 1C and 1D show the sensor arrangement 10 without the surrounding housing in a schematic sectional view and in a top view. The following description refers to all FIGS. 1A to 1D.

As shown in FIGS. 1A and 1B, the sensor arrangement 10 is situated inside the housing 10, which has an opening 12 connecting the interior of the housing 11 to the outside atmosphere. Through the opening 12, gas 990 of the surrounding gas atmosphere can enter the interior of the housing, as schematically depicted in FIG. 1A. Furthermore, when an external object 991 is placed in front of the opening 12, infrared radiation which, for example, is irradiated by a spot of a surface 992 of the external object 991, can enter the housing 11. In FIG. 1B, the infrared radiation is schematically indicated by reference numeral 993.

The sensor arrangement 10 comprises a first sensor unit 1 and a second sensor unit 2. Each of the sensor units 1, 2 comprises a heater element 3 and a temperature sensor element 4, respectively. According to the present embodiment, in each sensor unit 1, 2 the heater element 3 is the temperature sensor element 4, meaning that the heater element 3 and the temperature sensor element 4 are embodied as one and the same component, which is a combined heater and temperature sensor element 3, 4.

The combined heater and temperature sensor element 3, 4 comprises a filament, which, on the one hand, acts as a resistance heater upon appliance of a sufficiently high electrical current. For concentrating the produced heat in a desired area, a part of the filament is formed in a meander-like shape as can be seen in FIG. 1D. On the other hand, the filament changes its electrical resistance depending on its temperature, so that measuring the electrical resistance, or an electrical property depending on the electrical resistance, can provide information about the temperature of the combined heater and temperature sensor element 3, 4. Preferably, each of the sensor units 1, 2 comprises an NTC or PTC material. For example, the combined heater and temperature sensor element 3, 4 of each of the sensor units 1, 2 comprises a noble metal as, for example, Pt, which can be used as a heater material and which has a temperature-depending electrical resistance. For providing the electrical current to the combined heater and temperature sensor element 3, 4 when operated as heater and/or for measuring an electrical property of the heater and temperature sensor element 3, 4, the sensor units 1, 2 comprise electrical contacts 8.

The sensor units 1, 2 are arranged on a common substrate 6, which can be made, for example, from silicon. The combined heater and temperature sensor element 3, 4 is at least partly situated in a membrane, which can comprise or can be made of silicon oxide and/or silicon nitride and at least partly encloses the combined heater and temperature sensor element 3, 4. The membrane 7 has a thickness in the range of about 400 nm to 10 µm. The substrate 6 has openings in the regions, where the combined heater and temperature sensor element 3, 4 is situated so that the thermal mass of the sensor units 1, 2 is very low. The substrate 6 and/or the membrane 8 with the components arranged in the membrane 8 can be manufactured by standard MEMS (microelectromechanical systems) technology, thereby providing small dimensions of typically 2×2 mm$^2$ and a high degree of integration.

The first sensor unit 1 is embodied as a pellistor, in particular as a catalytic pellistor, and comprises a catalyst element 5 in the form of a pellet on the membrane 7. As can be seen in FIG. 1D, the catalyst element 5 is arranged on the meander-shaped part of the combined heater and temperature sensor element 3, 4, so that the catalyst element 5 can be effectively heated. The catalyst element 5 comprises or consists of a metal oxide, for instance with Al and/or Pt. For example, the catalyst element 5 can comprise or consist of platinum oxide and/or aluminum oxide or aluminum oxide mixed with platinum. The second sensor unit 2 is embodied similarly to the first sensor unit 1, but without the catalyst element 5.

As shown in FIGS. 1A and 1B, the housing 11 preferably completely encloses the first and second sensor units 1, 2 except for the opening 12 in the housing 11, so that the housing 11 has an interior space in which the sensor units 1, 2 are arranged. The interior space is connected to the environment only or at least substantially only through the opening 12. Preferably, the housing 11 has no further opening.

In the shown embodiment, by way of example the housing 11 comprises a housing body 13 carrying the sensor arrangement 10 and a cover element 14 covering the sensor arrangement, so that the opening 12 is situated over the second sensor unit 2. Both the housing body 13 and the cover element 14 can comprise a ceramic and/or plastics material. Alternatively, the cover element 14 can, for example, also comprise or consist of a metal. In the shown embodiment, the housing body 13 additionally comprises a heat distribution element 16, which can be made of a metal, so that both sensor units 1, 2 receive the same background radiation from the housing side opposite the cover element 14. Furthermore, the housing 11 comprises electrical connection elements 15, which are connected to the electrical contacts 8 of the sensor units 1, 2, for example, by wire connections, so that the sensor units 1, 2 can be contacted from outside the housing 11.

When operated in the first mode of operation, as shown in FIG. 1A, in both sensor units 1, 2 the respective heater element 3 is operated in order to heat both sensor units 1, 2. Preferably, an electrical current can be applied to each of the heater elements 3 which would heat the sensor units 1, 2 to the same or substantially the same temperature in the absence of a surrounding gas atmosphere. When heated to a temperature of typically at least 200° C. to at least 300° C., the catalyst element 5 combusts gas 990 surrounding the first sensor unit 1, thereby generating additional heat. That additional heat increases the temperature of the first sensor unit 1 in comparison to the temperature of the second sensor unit 2. Consequently, the combustion-generated additional heat produces a change in the electrical resistance of the temperature sensor element 4 of the first sensor unit 1, which is proportional to the gas concentration, in comparison to the electrical resistance of the temperature sensor element 4 of the second sensor unit 2. As becomes clear from FIG. 1C, the sensor units 1, 2 and the electrical contacts 8 form a voltage divider circuit. For example by means of a Wheatstone Bridge the change in the electrical resistance of the temperature sensor element 4 of the first sensor unit 1 in comparison to the second sensor unit 2 can be measured via the corresponding voltage difference. Consequently, in the first mode of operation the first sensor unit 1 is an "active" sensor, while the second sensor unit 2 works as a compensator. The advantage of this kind of circuit is that the sensor device 100 will only react to gas concentration changes. Other environmental changes as, for example, changes of the humidity and/or of the ambient temperature will be canceled.

When operated in the second mode of operation, as shown in FIG. 1B, neither of the heater elements 3 of the sensor units 1, 2 is operated. Thus, compared to the first mode of operation the heater elements 3 have no function in the second measurement mode. Since the opening 12, which is needed for the gas sensor mode of operation as described previously, is situated directly above the second sensor unit 2, infrared radiation 993 can enter the housing 11 through the opening 12 as explained above and heat the second sensor unit 2. Because the membrane 7 of the sensor units 1, 2 is very thin, the thermal mass of the sensor units 1, 2 is low and the membrane 7 of the second sensor unit 2, and thus the second sensor unit 2, is very fast in reaching a stable temperature equilibrium state with the infrared radiation 993. In contrast, the first sensor unit 1, which is covered by the cover 14 and thus shielded from the infrared radiation 993, is at equilibrium with the housing temperature. If an external object 991 as shown in FIG. 1B is placed in front of the opening 12 so that the second sensor unit 2 is exposed to the infrared radiation 993 emitted by the surface 992 of the external object 991, the temperature of the second sensor unit 2 changes due to the infrared radiation 993, while the first sensor unit 1 is shielded by the housing 11. Although the temperature of the housing 11 in principle can also change, there is a huge difference in the temperature change of the second sensor unit 2 in comparison to the temperature change of the first sensor unit 1. By measuring the electrical resistances of the temperature sensor elements 4 information about the temperature of the sensor units 1, 2 can be obtained.

The temperature of the measurement spot on an external object can be calculated as a function of the electrical resistance of the second sensor unit, the electrical resistance of the first sensor unit and the emissivity of the sample spot, which is the relevant part of the surface of the external object. As the temperature depends on infrared radiation flux between the sample spot and the sensor device, the temperature of the first sensor unit, which acts as a reference, is needed to calculate the external object's temperature properly.

Figure 2:
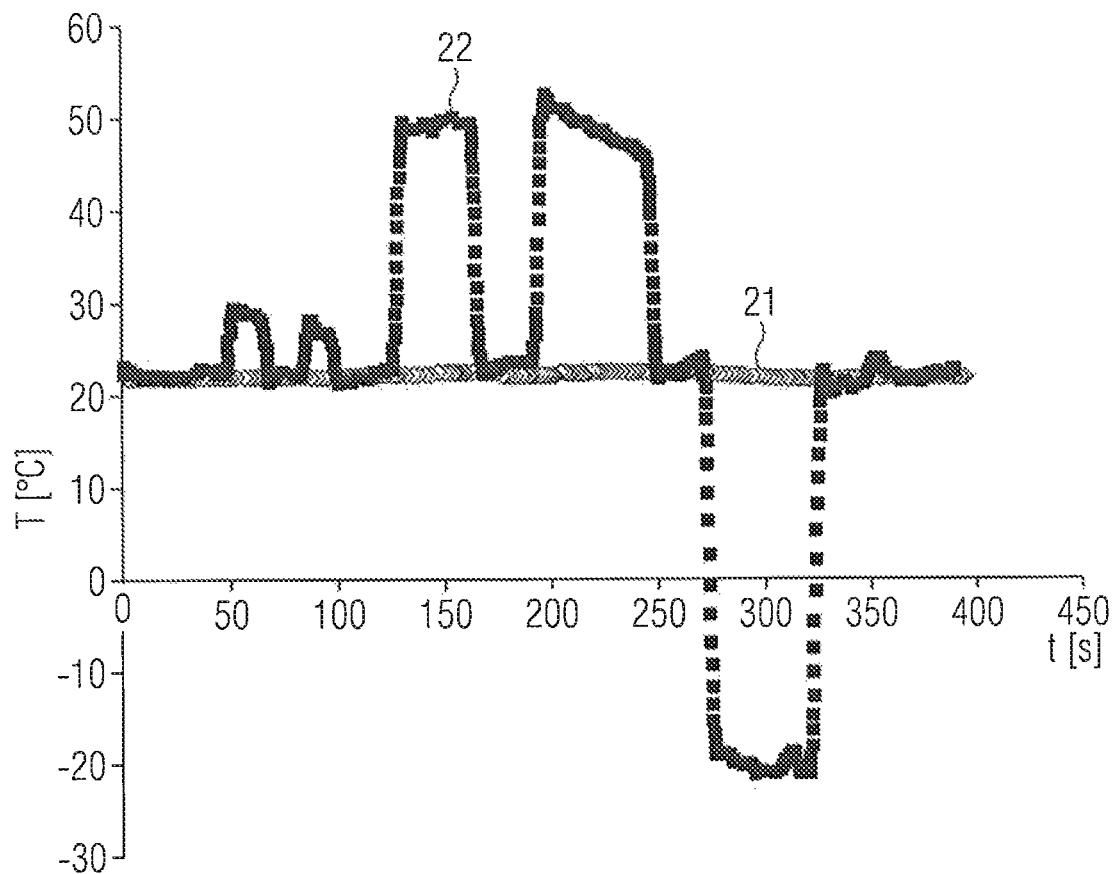
FIG. 2 shows a temperature measurement performed by the sensor device.

In FIG. 2 a graph is shown, which illustrates experimental measurements of the resistance changes of the temperature sensor elements 4 and thus the temperatures T of the sensor units 1, 2, respectively. The measurements were recorded during a time interval t. In that time interval, several external objects were placed one after the other in front of the sensor device, which initially had a temperature of about 22° C. The measurement points denoted by reference numeral 21 represent the readings from the first sensor unit, and the measurement points denoted by reference numeral 22 represent the readings from the second sensor unit. Between t=50 s and t=100 s a human hand and a human in clothes were arranged in front of the opening of the sensor device, respectively, resulting in temperature increases of the second sensor device of about 30° C. Between t=120 s and t=250 s an aluminum block and a wood block, both initially heated to a temperature of about 50° C., where placed in front of the sensor device, resulting in temperature increases of the second sensor device of about 50° C. The gradient during the measurement with the wood block between t=180 s and t=250 s is due to the worse heat conductivity and heat capacity of the wood block compared to the aluminum block. Between t=290 s and t=330 s an aluminum block, which was cooled to a temperature of about −20° C., was placed in front of the sensor device, resulting in a temperature drop of the second sensor device of about 40° C. In contrast to the strong temperature changes of the second sensor unit, the first sensor unit, measuring the housing temperature indicated temperature changes of less than about 1° C. during the described events, thereby proving the above-described shielding effect of the housing.

An exemplary method for using the sensor device 100 can be the following:

Operate the sensor device in a first method step in the first mode of operation by heating the heater elements of both the sensor units to a temperature of about 200° C. to 300° C. and measure the difference in electrical resistances of the temperature sensor elements by means of a voltage measurement in a Wheatstone Bridge using the voltage divider circuit provided by the electrical contacts. By using calibrated data the gas concentration of the surrounding gas atmosphere can be calculated.

Operate the sensor device in a second method step in the second mode of operation by switching off the heater elements of the sensor units and measuring the electrical resistances of the first and second sensor unit, respectively. By using another set of calibrated data, the sensor device temperature and the temperature of the measurement spot of an external object can be calculated.

The first and second method steps can be repeated afterwards. Furthermore, the order of first and second method steps can be changed.

Figure 3:
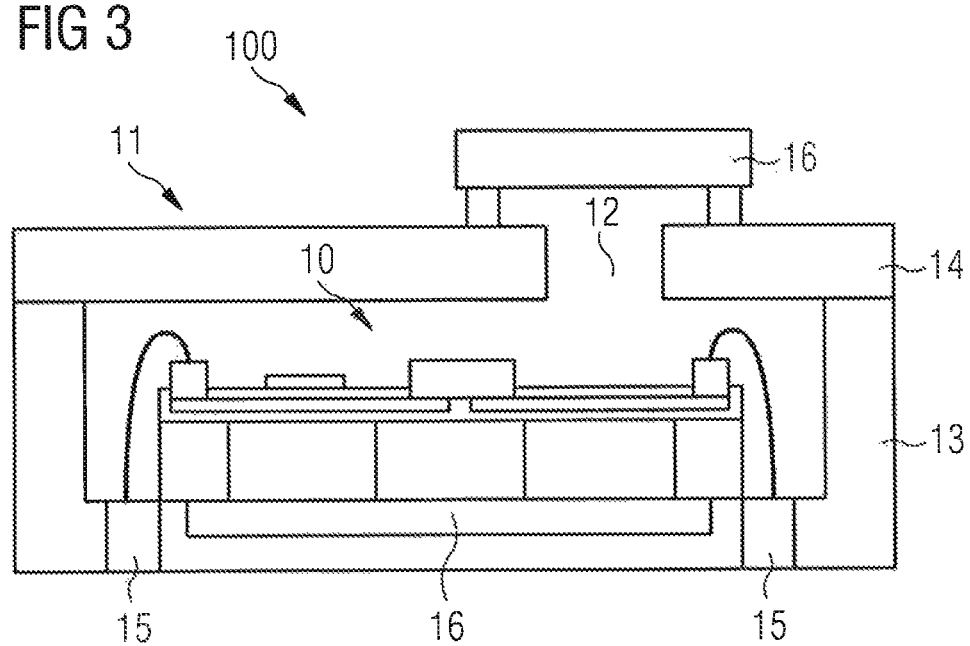
FIGS. 3 to 5 show schematic drawings of sensor devices according to further embodiments.

In order to improve the infrared measurement capability in the second mode of operation, an infrared lens 17 can be placed on the opening 12 of the housing 11, as shown in FIG. 3, illustrating a further embodiment of the sensor device 100. The lens 17 can comprise, for example, one or more materials chosen from Ge, ZnSe, ZnS, Si, CaF$_2$. The lens 17 can, for example, comprise a suitable support that ensures that the opening 12 is not blocked so that gas a gas exchange through the opening 12 remains possible.

Figure 4A:
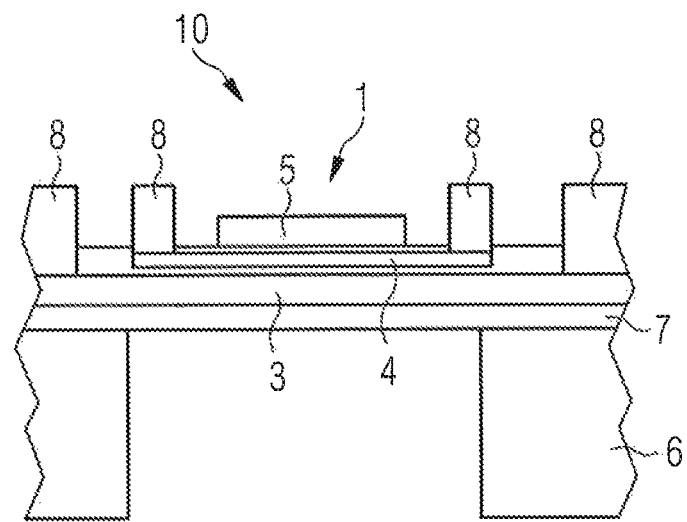
Figure 4B:
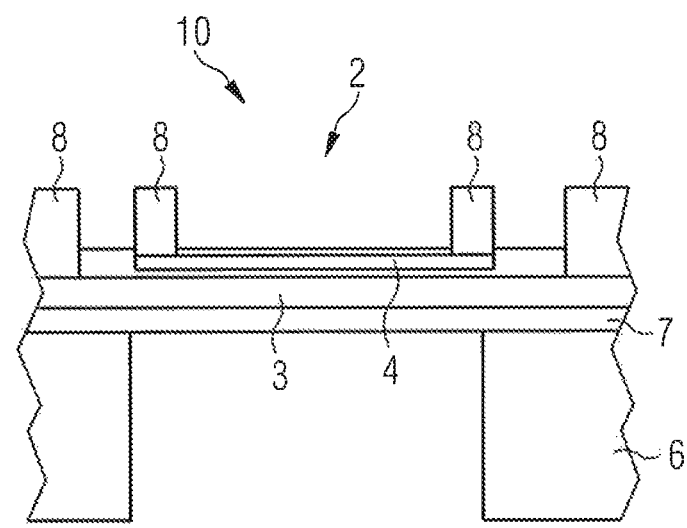

As described in connection with FIGS. 1A to 1D, the heater element 3 and the temperature sensor element 4 of each of the sensor units 1, 2 can be embodied as one and the same component, respectively. Alternatively, the sensor units 1, 2 can have a heater element 3 and a temperature sensor element 4, which are separate components, as shown in FIGS. 4A and 4B. The heater elements 3 and the temperature sensor elements 4 can be embodied as explained above and can all be arranged in the membrane 7. As shown, additional contact elements 8 can be provided for contacting the heater elements 3 and the temperature sensor elements 4 separately.

Figure 5:
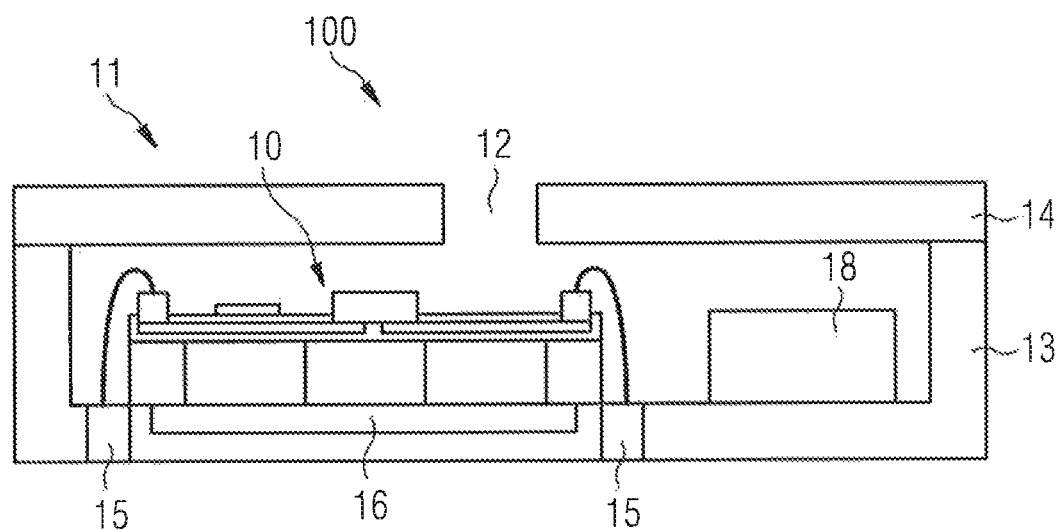

Furthermore, the sensor element 100 can comprise at least one additional electronic device 18, as shown in FIG. 5, which can be placed inside the housing 11 together with the sensor arrangement 10. The at least one electronic device 18 can, for example, comprise an integrated circuit as an ASIC for controlling the sensor units and operating the sensor device in the first and second mode of operation.

Figure 6:
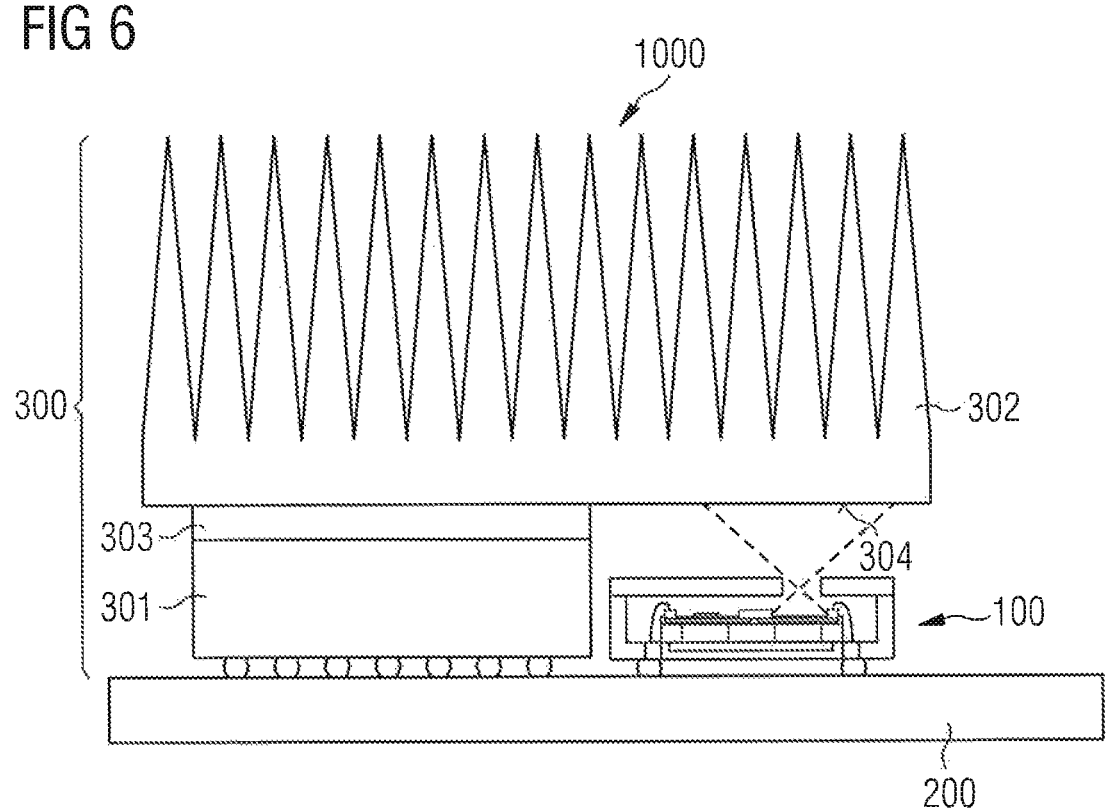
FIG. 6 shows a schematic drawing of an electronic assembly with a sensor device according to a further embodiment.

FIG. 6 shows an embodiment of an electronic assembly 1000 comprising a sensor device 100 which can be embodied as explained before. The electronic assembly 1000 further comprises an electronic component 300. The electronic component 300 and the sensor device 100 can be placed on a common carrier 200 as, for example, a printed circuit board (PCB). By way of example, the electronic component 300 can comprise an active electronic component 301 as, for instance, an integrated circuit like a processor, which is thermally connected to a heat sink 302 via a heat conductor 303. The sensor device 100 is arranged on the carrier 200 so that the second sensor unit faces a surface 304 of the electronic component 300 through the opening in the housing. As shown in FIG. 6, the surface 304 of the electronic component 300 faced by the second sensor unit can be a surface of the heat sink 302. Alternatively, it can also be a surface of the active electronic component 301. By operating the sensor device 100 in the described first and second modes of operation, the sensor device 100 can be used to measure information about a gas in the vicinity of the electronic component 300 in the first mode of operation and information about a temperature of the electronic component 300 in the second mode of operation.

Alternatively or additionally to the features described in connection with the figures, the embodiments shown in the figures can comprise further features described in the general part of the description. Moreover, features and embodiments of the figures can be combined with each other, even if such combination is not explicitly described.

The invention is not restricted by the description on the basis of the exemplary embodiments. Rather, the invention encompasses any new feature and also any combination of features, which in particular comprises any combination of features in the patent claims, even if this feature or this combination itself is not explicitly specified in the patent claims or exemplary embodiments.

What is claimed is:

1. A sensor device comprising:
   a first sensor unit and a second sensor unit in a common housing,
   wherein each of the first and second sensor units comprises a heater element and a temperature sensor element,
   wherein the housing comprises a cover element having an opening, the cover element covering the first sensor unit, and
   wherein the opening is arranged over the second sensor unit.

2. The sensor device according to claim 1, wherein an interior space of the housing, in which the first and second sensor units are arranged, is connected to an environment through the opening, and wherein the opening is configured to let a gas to be examined enter the housing.

3. The sensor device according to claim 2, wherein the interior space is connected to the environment only or at least substantially only through the opening and the housing has no other opening.

4. The sensor device according to claim 1, wherein the housing, except for the opening over the second sensor unit, completely encloses the first and second sensor units.

5. The sensor device according to claim 1, wherein the first sensor unit and/or the second sensor unit is a pellistor.

6. The sensor device according to claim 1, wherein the first sensor unit comprises a catalyst element.

7. The sensor device according to claim 1, wherein the temperature sensor element of at least one of the first sensor unit or the second sensor unit comprises an NTC or PTC material.

8. The sensor device according to claim 1, wherein the temperature sensor element and/or the heater element of at least one of the first sensor unit or the second sensor unit comprises a noble metal.

9. The sensor device according to claim 8, wherein the noble metal comprises Pt.

10. The sensor device according to claim 1, wherein in at least one of the first sensor unit or the second sensor unit the heater element is the temperature sensor element.

11. The sensor device according to claim 1, wherein the sensor device comprises a common substrate carrying both the first and second sensor units.

12. The sensor device according to claim 11, wherein in at least one of the first sensor unit or the second sensor unit the temperature sensor element and/or the heater element is arranged in a membrane, which is arranged on the substrate.

13. The sensor device according to claim 12, wherein the first sensor unit comprises a catalyst element and the catalyst element is arranged on the membrane.

14. The sensor device according to one of claim 12, wherein the membrane of at least one of the first sensor unit or the second sensor unit comprises a silicon oxide and/or silicon nitride and at least partly encloses the heater element and/or the temperature sensor element.

15. The sensor device according to one of claim 11, wherein the substrate comprises silicon.

16. An electronic assembly comprising:
   a common carrier;
   an electronic component disposed on the carrier; and
   the sensor device according to claim 1 disposed on the carrier,
   wherein the second sensor unit faces a surface of the electronic component through the opening in the housing.

17. A method for operating the sensor device according to claim 1, the method comprising:
   operating the sensor device as a gas sensor in a first mode of operation; and
   operating the sensor device as an infrared sensor in a second mode of operation.

18. The method according to claim 17, wherein both the first and second sensor units are operated in both the first and second modes of operation, respectively.

19. The method according to claim 17,
    wherein, in the first mode of operation, the heater element of each of the first and second sensor units is operated to heat the respective sensor unit, and
    wherein, in the second mode of operation, the heater element of each of the first and second sensor units is not operated to heat the respective sensor unit.

20. The method according to claim 17,
    wherein, in the first mode of operation, the second sensor unit is operated as a reference sensor, and
    wherein, in the second mode of operation, the first sensor unit is operated as a reference sensor.

\* \* \* \* \*